United States Patent [19]

Emura et al.

[11] Patent Number: 4,885,178

[45] Date of Patent: Dec. 5, 1989

[54] METHOD OF MAKING A SOYBEAN PROTEIN FOOD PRODUCT

[75] Inventors: Tatuo Emura, Sapporo; Kiyoshi Ohba, Chitose, both of Japan

[73] Assignee: Kabushiki Kaisha Hokkaido Nissin, Hokkaido, Japan

[21] Appl. No.: 167,508

[22] Filed: Mar. 14, 1988

[51] Int. Cl.$^4$ .............................. A23J 3/00; A23L 1/20
[52] U.S. Cl. ........................................ 426/46; 426/52; 426/634; 426/656; 426/573; 435/221; 435/252.5
[58] Field of Search ............... 426/49, 52, 46, 43, 426/656, 634, 573; 435/221, 252.5

[56] References Cited

U.S. PATENT DOCUMENTS

| | | | |
|---|---|---|---|
| 3,640,725 | 2/1972 | Sherba et al. | 426/46 |
| 3,857,970 | 12/1974 | Tsumura et al. | 426/46 |
| 4,100,024 | 7/1978 | Adler-Nissen | 426/46 |
| 4,324,805 | 4/1982 | Olsen | 426/46 |

Primary Examiner—Marianne Cintins
Attorney, Agent, or Firm—Browdy and Neimark

[57] ABSTRACT

A soybean protein food product made by use of a newly discovered microorganism which releases a soybean protein clotting enzyme, and a method of making such soybean protein food product is disclosed. The new enzyme functions to clot a soybean protein (soymilk), thus permitting an effective production of new fermented soybean products, such as a soymilk cheese or a soymilk cream, as well as any other wide varieties of soybean protein food products.

3 Claims, 4 Drawing Sheets

METHOD OF MAKING A SOYBEAN PROTEIN FOOD PRODUCT

BACKGROUND OF THE INVENTION

1. Field of the Invention

The present invention relates to a soybean protein product and method of producing the same, and in particular, to a soybean protein clotting enzyme which is utilized in the process of producing a soybean protein product, a method of producing the soybean protein clotting enzyme effeciently, and a method of making a soybean protein food product by use of a soybean protein clotting enzyme.

2. Description of the Prior Art

In recent years, a vegetable food has received a great attention from many people having an increased concern about their health in view of the tendency for most of people to eat an excessive amount of animal foods or fats being the cause of such fatal diseases as heart diseases, or arteriosclerosis.

Generally, most of commonly available vegetable food products are artificially made from vegetable oils and fats, as quasi-vegetable foods, and as such, a pure vegetable food product is not available easily from local shops, nowadays.

Among other vegetables, a soybean is, not to mention its high quality of vegetable protein, a major food that has long been utilized in a variety of food products, and is said to contain almost all essential nutrition for human health.

Study and development have been made in an attempt to use a soybean protein for production of a pure vegetable food. However, a difficulty has still remained in producing a fermented soybean protein food similar to a cheese which is made from milk. The reason is that a cheese is produced via a rennin enzyme which clots milk proteins, but nobody has hitherto discovered an enzyme capable of clotting the soybean proteins in a manner analogous to such rennin enzyme.

SUMMARY OF THE INVENTION

It is a primary purpose of the present invention to provide a novel soybean protein food product.

In accomplishment of this purpose, in accordance with the present invention, a bacteria is discovered by the inventor, which is deemed to belong to the genus Bacillus and releases a soybean protein clotting enzyme. The bacteria is name 26D7. It is therefore found that the addition of such enzyme released by the 26D7 into a soybean protein permits an effective production of a new soybean protein food, such as for example, a soymilk cheese or a soymilk cream.

It is another purpose of the present invention to provide a method of producing a soybean protein clotting enzyme efficiently.

In achieving this purpose, in accordance with the present invention, the above-mentioned bacteria (26D7) is cultured at a medium comprising 0.1% yeast extract, 0.02% casamino acid, 0.1% ammonium sulfate, 0.05% sodium citrate, 0.01% magnesium sulfate, 1.0% phosphate, and 5.0% soymilk (adjusted to pH6.0 by addition of KOH).

Accordingly, in the presence of 5.0% soymilk, the strain 26D7 is found to produce a sufficient activity of a soybean protein clotting enzyme so as to clot the soymilk in a satisfactory manner.

It is still another purpose of the present invention to provide a soybean protein clotting enzyme per se which is effective for clotting a soybean protein.

To this end, in accordance with the present invention, there is obtained a soybean protein clotting enzyme of the following characteristics.

Molecular weight: approx. 30000
Optimal temperature: approx. 80° C.
Thermal stability: stable at 35° C.–40° C. for 30 min.
Optimal pH: below pH 6.0
pH stability: stable at pH4–pH9 for 12 h.
Influence of metal ions: null
Influence of inhibitors: enzymatic activity is halted by phenyl methyl sulfonyl fluoride and tosyl fluoride.
Proteolytic activity and enzyme: a sort of serine protease

DETAILED DESCRIPTION OF PREFERRED EMBODIMETNS OF THE INVENTION

Firstly, we, the inventors of the present invention, effected a number of screening procedures in order to find a microorganism, or a bacteria capable of releasing a soybean protein clotting enzyme. Soils and plants were mainly collected and subjected to screening procedures in a known conventional way.

As a result, we discovered and succeeded in isolating a new bacteria with the property of releasing a soybean protein clotting enzyme in the presence of a soybean protein, and hereby let it be known that the bacteria strain is named 26D7 and has been deposited under the deposit number FERM BP-1778 at the authorized Japanese depositary, Agency of Industrial Science and Technology, with its address at 1-3, Higashi 1-chome, Tsukuba-shi, Ibaraki-ken, Japan, in conformity with the provisions of Butapest Treaty on the international recognition of the deposit of microorganisms for the purposes of patent procedure.

Now, description will be given of the bacterial properties and culture of the above-mentioned strain 26D7.

CULTURE MEDIUM

The microorganism identified as 26D7 was cultured in a medium prepared from the ingredients shown in the Table 1 below.

TABLE 1

| Beef extract | 10 g |
|---|---|
| Polypeptone | 10 g |
| NaCl | 5 g |
| Distilled water | 1000 ml |

The foregoing medium may be formed on a plate as a plate medium by addition of 1.5% agar thereinto.

BACTERIAL PROPERTIES

Thus-cultured strain 26D7 was determined its bacterial properties. The results are shown in the Table 2 below.

TABLE 2

| Shape | rod |
|---|---|
| Sporulation | + |
| Gram staining | + |
| Growth at 45° C. | + |
| 65° C. | − |
| Growth in 7% NaCl | + |
| Voges-Proskaver reaction | + |
| Catalase | + |
| Growth in anaerobic state | + |
| Motility | +++ |
| Utilization of carbohydrate glucose± | + |

The above results suggest that the strain 26D7 in question might belong to the genus Bacillus.

Next, description will be made in regard to a a soybean protein clotting enzyme release by the 26D7, and procedures for isolating and purifying such enzyme, hereinafter.

The first stage for encouraging the aforementioned strain 26D7 to produce soybean protein clotting enzymes is such that the strain 26D7 is cultured in a best preferred medium prepared in accordance with the Table 3 below. Or alternatively, any other kinds of media may be used, which contains a required nutrition sources, including nitrogen and carbon sources, insofar as the media per se contain nitrogen source (soybean protein) and phosphate. It is important that nitrogen source (soybean protein) and phosphate must be added in the medium in order to insure the release of soybean protein clotting enzymes from the bacteria 26D7, which function to cloth the soymilk in this instance.

TABLE 3

| Yeast extract | 0.1% |
|---|---|
| Casamino acid | 0.02% |
| Ammonium sulfate | 0.1% |
| Phosphate | 1.0% |
| Sodium citrate | 0.05% |
| Magnesium sulfate | 0.01% |
| Soymilk | 5.0% |

Note: Adjusted to pH 6.0 by adding KOH.

Figure 1:
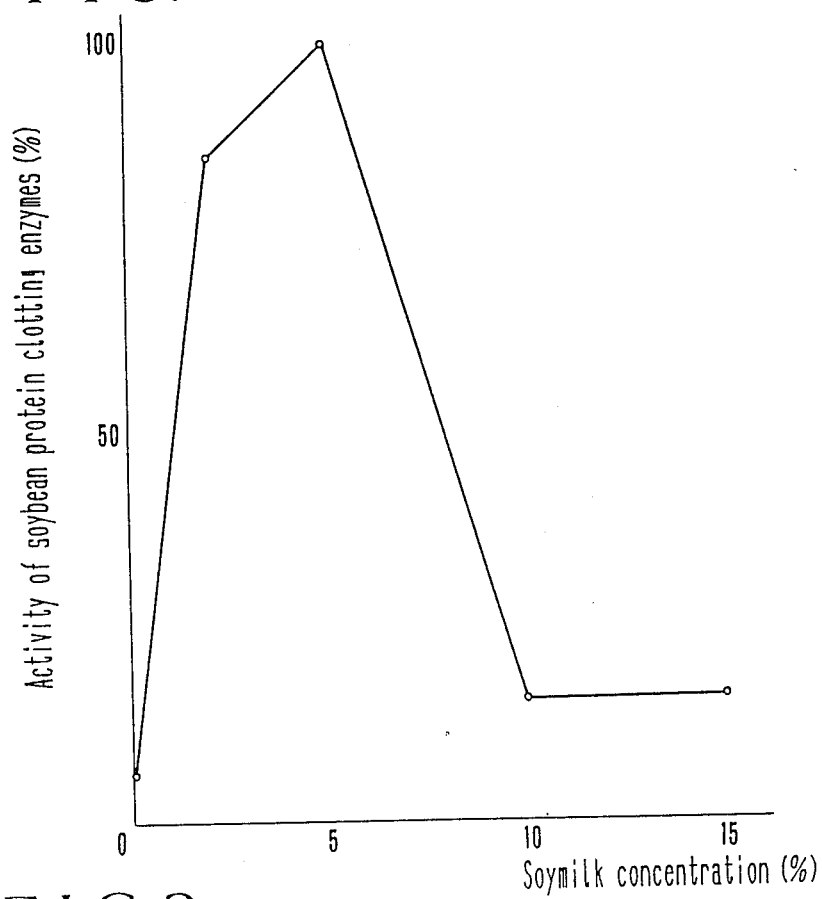
FIG. 1 is a graph showing the activity of a soybean protein clotting enzyme in relation to a soymilk concentration in a culture medium.

Regarding the above-listed composition of medium in Table 3, it is preferable that the concentration of the soymilk should srictly be set at 5.0% as above, since experiments show that the soymilk concentration below or above 5.0% results in the reduced production of the soybean protein clotting enzyme as understandable from FIG. 1.

The strain 26D7 was inoculated into the above-mentioned medium, and cultured therein in an aerobic condition by means of a conventional shaking-type aeration and agitation device at the temperature of 45° C. for 48–72 hours. In terms of the aeration, care must be taken to control the air supply amount in the medium at a moderate degree, avoiding an excessive larger or lower amount of air supplied, because it adversely affects the productivity of the soybean protein clotting enzyme. Preferably, the aeration and agitation should be carried out by a suitable rotary shaker at 200–400 rpm, keeping the air supply at 0.5–0.8 VVm.

Figure 2:
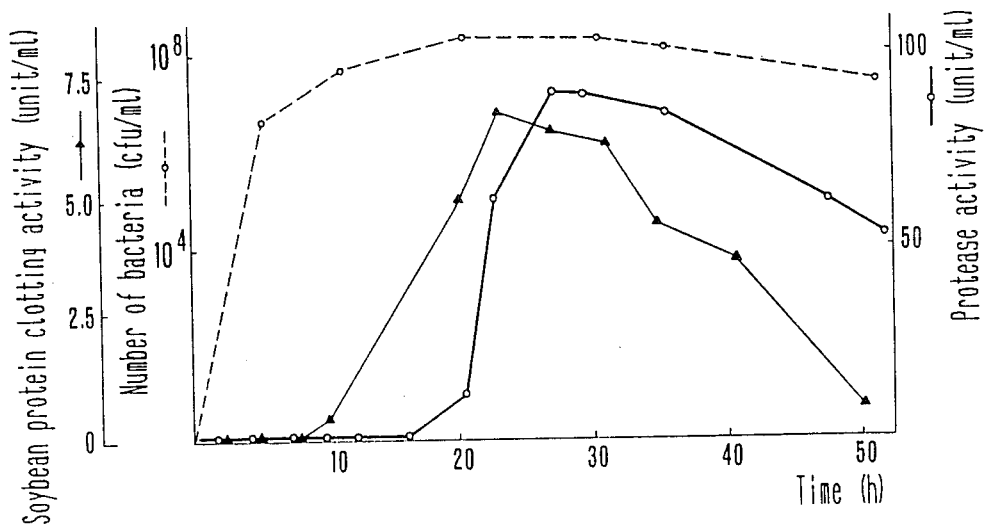
FIG. 2 is a graph showing the relation between bacteria growth and soybean protein clotting enzyme activity, in which also shown is the proteolytic activity of the same soybean portein clotting enzyme.

Under those conditions, the 26D7 was grown and soybean protein clotting enzymes were produced, as shown in FIG. 2. In this connection, we also determined the proteolytic activity of the same soybean protein clotting enzymes, for the sake of comparison between the soybean protein clotting activity and proteolytic activity of the soybean protein clotting enzymes.

After the above-described culture of 26D7, the purification and isolation of the soybean protein clotting enzyme were conducted, which will be set forth below.

The cultured medium (in liquid) was filtered through a kieselguhr, and a residual layer on the kieselguhr, which contains crude soybean protein clotting enzymes, was injected into a 55% saturated ammonium sulfate solution for precipitation purpose. Thereafter, the precipitate of crude soybean protein clotting enzymes was desalted by a gel filtration chromatography using a Sephadex G25 gel column (available from Pharmacia Fine Chemicals) to thereby obtain the fractions of the crude soybean protein clotting enzymes.

Figure 3:
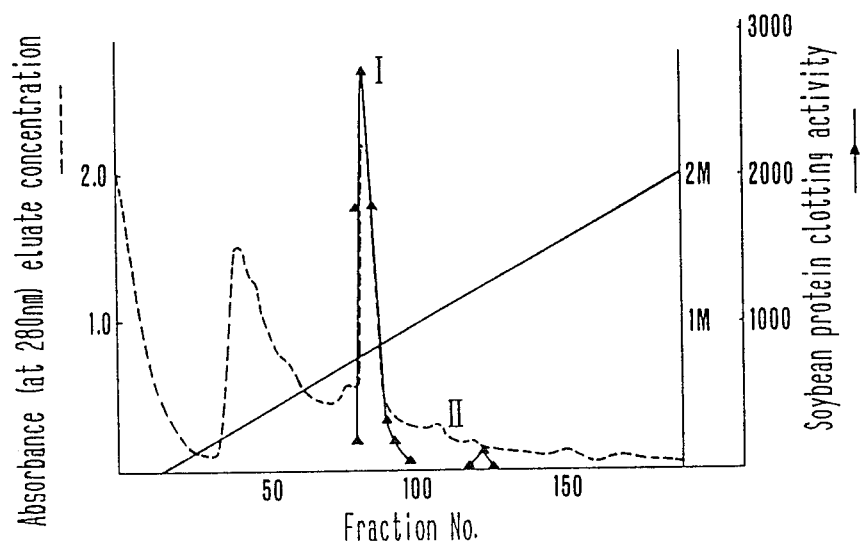
FIG. 3 is a graph showing the optical measurement results of crude enzyme fractions eluted through a CM-cellulose column chromatography in accordance with a NaCl linear gradient, and also showing the respective peak activities of first and second soybean protein clotting enzyme fractions groups (I) and (II)

The desalted enzyme fractions were purified chromatographically using a CM-cellulose column (Pharmacia Fine Chemicals). Specifically, after the desalted fractions were chromatographed on such cellulose powder column, an appropriate volume (3–5 ml) of different NaCl solutions with gradually different NaCl concentrations ranged from 0M to 2M were prepared so that a linear NaCl gradient was provided for obtaining multiple fractions in accordance with the NaCl linear gradient. Then, by dispensing each of such different NaCl solutions into the column, each eluate dropped from the column was received in a cell, so that plural cells of eluate were prepared and labelled their respective fraction numbers. Then, the eluate cells were measured by a spectrophotometer at 280 nm. The resultant absorbance of each eluate is shown by the dotted line in FIG. 3, which reveals the peak absorbace values at the fraction Nos. 75–100. On the other hand, the activity of the soybean protein clotting enzymes was determined at each of those eluate cells, with the result that the enzymatic activity (-▲-) was observed substantially at the fraction Nos. 75–100 as a first peak fraction group (I), thus coinciding with the foregoing peak absorbance values of the same eluate, and further observed substantially at fraction Nos. 120-130 as a second peak fraction group (II), as shown in FIG. 3.

Accordingly, it is seen that the soybean protein clotting enzymes exist at the fraction Nos. 75-100 as well as 120-130.

Figure 4:
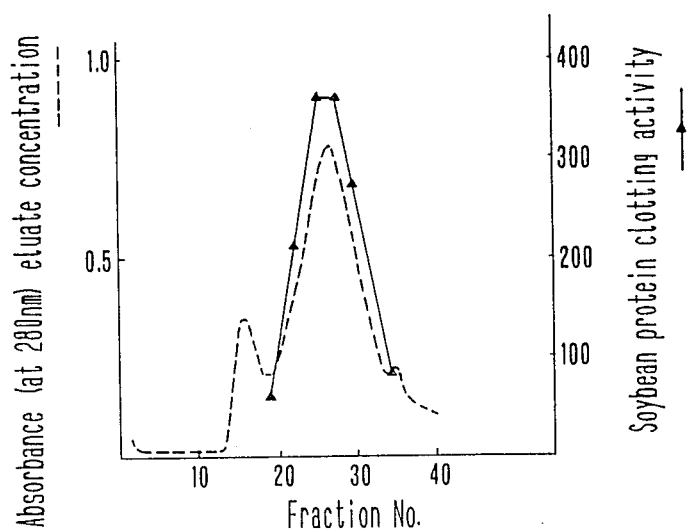
FIG. 4 is a graph showing the optical measurement results of further purified fractions of soybean protein clotting enzymes corresponding to the first fraction group (I) in the FIG. 3.

Next, the eluate in the cells with those fraction Nos. 75-100 and 120-130 were furthermore purified by a gel filtration chromatography using Sephadex G-100 gel column (Pharmacia Fine Chemicals) in order to obtain an isolated soybean protein clotting enzyme. Each eluate therefrom was renumbered its fraction number and measured its absorbance at 280 nm and determined the activity of the soybean protein clotting enzyme. The results are shown in FIG. 4, and the chromatogram of the first peak fraction group (I) on this Sephadex G-100 gel column represents a single band pattern in a sense similar to that developed by SDS electrophoresis. The measurement of such fraction group (I) indictates that the molecular weight of the isolated soybean protein clotting enzyme is approximately 30000.

Figure 5A:
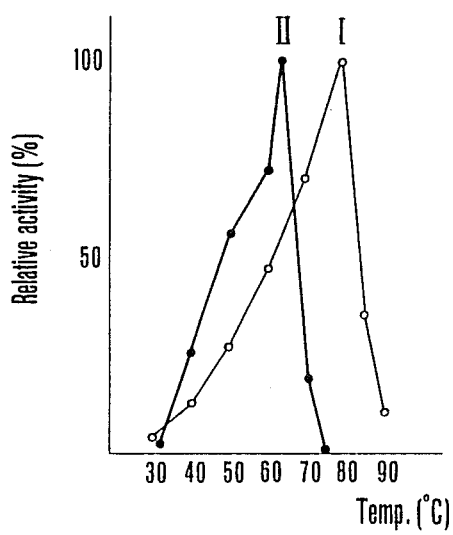
FIG. 5(A) is a graph showing an optimal temperature range for the respective activities of the first and second soybean protein clotting enzyme fraction groups (I) and (II)
Figure 5B:
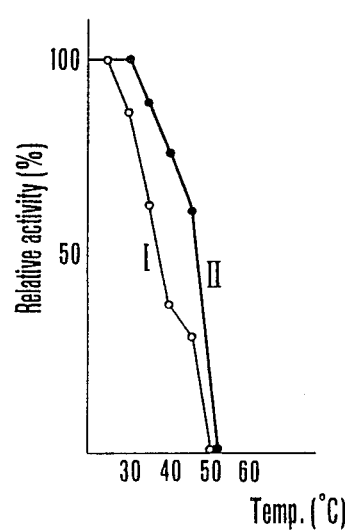
FIG. 5(B) is a graph showing a thermal stability range for the respective activities of the first and second soybean protein clotting enzyme fraction groups (I) and (II)

The optimal temperature range and thermal stability for the peak acitivity of the above-discussed soybean protein clotting enzymes were examined, and the results are shown in FIGS. 5(A) and 5(B), respectively. It is observed that the optimal acitvity temperature for the enzymes at the first peak fraction group (I) is approx. 80° C., whereas as for the crude enzymes at the second peak fraction group (II), the optimal activity temperature thereof is approx. 65° C., as in FIG. 5(A), and that, in terms of the thermal stability, the finally isolated enzyme obtained by the Sephadex G-100 stands stable at 35°-40° C. for 30 min., as in FIG. 5(B).

Figure 6A:
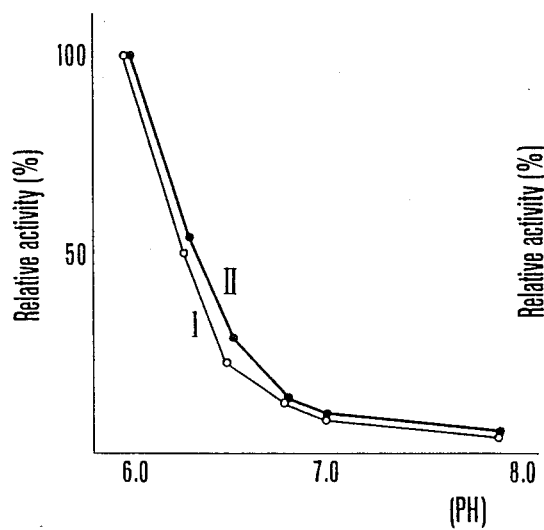
FIG. 6(A) is a graph showing a pH effect on the respective activities of the first and second soybean protein clotting enzyme fraction groups (I) and (II)
Figure 6B:
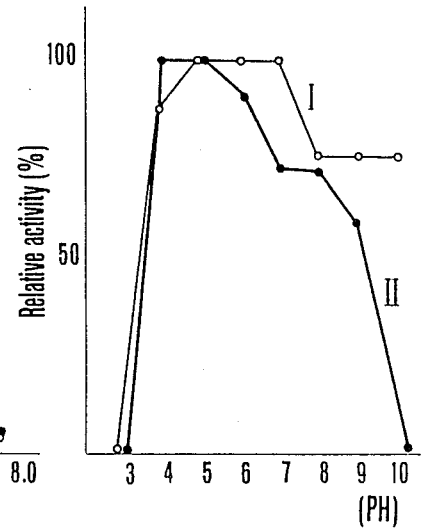
FIG. 6(B) is a graph showing a pH stability range for the respective activities of the first and second soymilk clotting enzyme fraction groups (I) and (II)

The pH effect and pH stability of the soybean protein clotting enzymes at the first and second peak fraction groups (I) and (II) were determined, and the results are shown in FIGS. 6(A) and 6(B). From FIG. 6(A), it is noted that the optimal pH range for the enzyme activity at both peak fractions (I) and (II) lies below pH 6.5, while on the contrary, at the pH level above pH 6.5, most of the enzyme activity is terminated. The pH stability of the enzymes at those peak fraction groups, as in FIG. 6(B) is maintained at pH 4 to pH 9; in other words, at the pH ranges from pH 4 to pH 9, about 70% of both enzymes remains alive and active for 17 hours at the temperature of 4° C.

Further, the influence of metal ions and inhibitors upon the soybean protein clotting enzymes was examined, and as a result thereof, there was almost no metal ion influence on both of the soybean protein clotting enzymes at the first and second peak fraction groups (I) and (II), but, according to the inhibitor experiments, the clotting activity of the enzyme at the first fraction group (I) was completely inhibited by phenyl methyl sulfonyl fluoride (PMSF) and tosyl fluoride (TSF), whereas only by ethylene diamine tetra-acetic acid (EDTA), was completely inhibited the clotting activity of the enzyme at the second peak fraction group (II). This result of inhibitor experiments indicates that the first peak fraction group (I) contains a kind of serine protease and the second peak fraction group (II) contains a kind of metal protease. The details of those metal and inhibitor experiments are shown in the Table 4 below.

TABLE 4

| Chemicals | Conc.(M) | Relative activity (%) (I) | (II) |
| --- | --- | --- | --- |
| $ZnSO_4$ $7H_2O$ | $1 \times 10^{-3}$ | 100 | 100 |
| $CuSO_4$ $5H_2O$ | " | 100 | 93.3 |
| $MgCl_2$ $6H_2O$ | " | 94.3 | 96.4 |
| $MnSO_4$ $4H_2O$ | " | 100 | 100 |
| $CaCl_2$ $2H_2O$ | " | 91.6 | 100 |
| $BaCl_2$ $2H_2O$ | " | 100 | 100 |
| $FeSO_4$ $7H_2O$ | " | 100 | 96.2 |
| $LiOH$ $H_2O$ | " | 100 | 100 |
| $HgCl_2$ | " | 100 | 90.2 |
| TSF | $1 \times 10^{-2}$ | 0 | 100 |
| EDTA | " | 100 | 0 |
| PMSF | " | 0 | 100 |
| None | | 100 | 100 |

Figure 7:
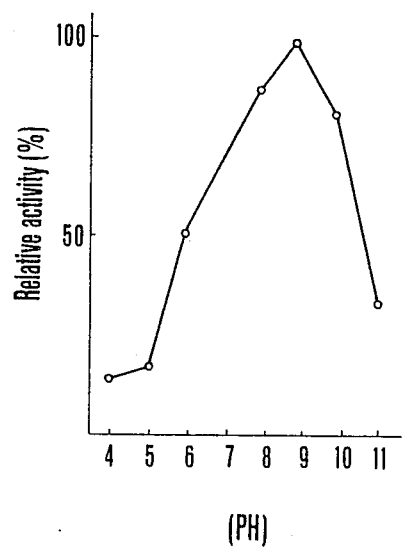
FIG. 7 is a graph showing an optimal pH range for the proteolytic activity of an isolated soybean protein clotting enzyme.
Figure 8:
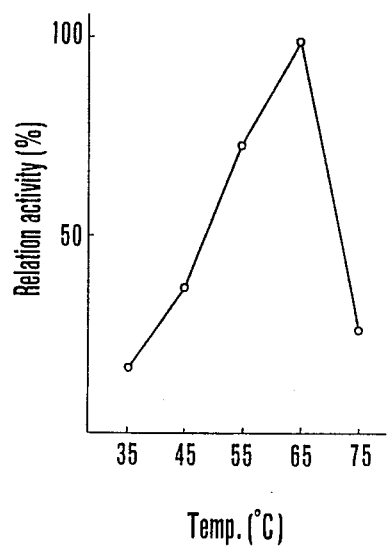
FIG. 8 is a graph showing an optimal temperature range for the proteolytic activity of an isolated soybean protein clotting enzyme.

FIGS. 7 and 8 are intended to show the optimal pH range and temperature for the proteolytic activity of the isolated soybean protein clotting eznyme, respectively.

METHOD OF PRODUCING A SOYBEAN PROTEIN FOOD

Now, we will describe the method of producing a cheese-like soybean protein food, as one of the preferred embodiments, by use of the above-stated soybean protein clotting enzyme.

In accordance with the present invention, a best preferred method for making such chees-like food involves, at first, preparing a base material by admixing the undermentioned items, and sterilizing the base material by a heating treatment at 80° C. for 30 min.

(a) Soybean protein solution prepared by liquifying a soybean protein powder so that the soybean protein concentration amounts to 7.5%.
(b) Lactose: 2%
(c) Fat: 25% (as a solid fat)
(d) Emulsifier: 2% against the fat While in the present embodiment, the soybean protein powder is utilized, it should be understood that a soymilk commonly on the market, or a soymilk for industrial use in other soybean food products, may also be utilized.

During the heat sterilizing treatment, the soybean protein is denatured.

Thereafter, the aforementioned base material is homogenized by means of a suitable homogenizer at 150 kg/cm$^2$ at the temperature of 70° C., and then, the hogenized base material is placed in a suitable thermostat or thermostatic vessel (such as a cheese fermentation vessel) and maintained therein at the temperature of 40° C. (preferably under the conditions of pH 6.5-6.6 and approx. 0.2 acidity). At this step, 2-3% lactic acid bacteria starter (pH 4.5-pH4.7 and 0.2-0.75 acidity) is added into the the thermostatic vessel. The base material is let stand under this condition for about 30 min.

Meanwhile, a soybean protein clotting enzyme solution is prepared by adding 0.03-0.06% enzyme powder of the previously described soybean protein clotting enzyme into 0.2M NaCl solution.

When the pH and acidity conditions in the thermostatic vessel becomes at pH 6.4-4.7 and about 0.25, respectively, the soybean protein clotting enzyme solution is injected into the vessel, whereupon the base material becomes clotted into a curd by virtue of the soymilk in the base material being clotted by the soybean protein clotting enzyme.

The base material is transformed into a cheese-like curd for about 2 hr. and 30 min, and when it is acertained that the curd state of the base material reached at a proper degree, the curd is cut into a predetermined pieces, and each pieces of curd is left as it stands for about 30 min., allowing separation of a whey therefrom.

Thereafter, the curd is mounted onto a mold device (a hoop) comprising a flat upper die and a lower die of a substantially top-opened cubic shape having plual holes perforated in its lateral walls and bottom wall, and then, after placing the curd in the lower die, the upper die is lowered down into the lower die, to thereby press the curd, forcing out water from the curd through the plural holes of the lower die.

At this stage, it is important to note that variations of the pressure against the curd provide a number of different natures of fermented soybean protein food products. For example, to keep applying a pressure of 4-5 kg/cm$^2$ to the curd for about 10 hours at the ambient temperature of 12°-15° C. results in producing a soft cheese-like soybean protein food product. A hard cheese-like food product, or a yogurt-like food product may be made by adjustment of pressure against the curd, as desired. In addition, a soybean protein cream may be produced if the lactic acid bacteria is not added. Moreover, addition of a flavor or other seasoning may avoid a bitter taste inherent in this fermented food product, and give a more smooth taste thereto.

While having described the present invention as above, it should be understood that the invention is not limited to the illustrated embodiments, but other replacements, modifications, or additions may be possible without departing from the scope and spirit of the appended claims for the invention.

Accordingly, from the above description, it is to be appreciated that the soybean protein clotting enzymes in accordance with the present invention is quite effective in clotting a soymilk or other soybean proteins, and may find use in a great wide variety of applications for producing many new soybean protein food products.

What is claimed is:

1. A method of producing a soybean protein food product comprising the steps of:
    preparing a soybean protein solution by liquifying a soybean protein powder so that the soybean concentration amounts to 7.5%;
    admixing 2% lactose, 25% solid fat, and 2% emulsifier based upon said fat, with said soybean portein solusion, to thereby provide a base material;
    sterilizing said base material by heating the same at 80° C. for 30 min.;
    thereafter, homogenizing said base material at a pressure of 150 kg/cm$^2$ at a temperature of 70° C.;
    then, placing said base material in a thermostatic container, and maintaining it therein at a temperature of 40° C. under a pH condition of pH 6.5-pH 6.6 and approximately 0.2 acidity;
    adding 2-3% lactic acid bacteria under a pH condition of pH 4.5-pH 4.7 and approximately 0.75 acidity;
    leaving said base material for about 30 min.;
    preparing a soybean protein clotting enzyme solution by adding 0.03-0.06% powdered soybean protein clotting enzyme into 0.2M NaCl solution;
    when said pH and acidity is about pH 6.4 and about 0.2-0.25, respectively, adding said soybean protein clotting enzyme solution into said base material;
    thereafter, when said base material is clotted into a curd, cutting said curd into plural pieces and leaving them to stand for about 30 min., allowing separation of a whey therefrom;
    thereafter, mounting said plural pieces of curd onto a mold device comprising a flat upper die and a lower die of a substantially top-ended cubic shape having plural holes perforated in its lateral walls and bottom wall; and
    lowering said upper die downwardly into said lower die, to thereby press said curd at a pressure of 4-5 kg/cm$^2$ for about 10 hrs. at an ambient temperature of 12°-15° C.

2. The method of producing a soybean protein food product according to claim 1, wherein said method further includes the step of adding a flavor into said curd after completion of pressing of said upper die against said curd.

3. A method of producing a soybean protein food product comprising the steps of:
    preparing a soybean protein solution by liquifying a soybean protein powder so that the soybean concentration amounts to 7.5%;
    admixing 2% lactose, 25% solid fat, and 2% emulsifier based upon said fat, with said soybean portein solusion, to thereby provide a base material;
    sterilizing said base material by heating the same at 80° C. for 30 min.;
    thereafter, homogenizing said base material at a pressure of 150 kg/cm$^2$ at a temperature of 70° C.;
    then, placing said base material in a thermostatic container, and maintaining it therein at a temperature of 40° C. uner a pH condition of pH 6.5-pH 6.6 and approximately 0.2 acidity;
    leaving said base material for about 30 min.;
    preparing a soybean protein clotting enzyme solution by adding 0.03-0.06% powdered soybean protein clotting enzyme into 0.2M NaCl solution and adding said soybean protein clotting enzyme into said base material;
    thereafter, when said base material is clotted into a curd, cutting said curd into plural pieces and leaving them to stand for about 30 min., allowing separation of a whey therefrom;
    thereafter, mounting said plural pieces of curd onto a mold device comprising a flat upper die and a lower die of a substantially top-ended cubic shape having plural holes perforated in its lateral walls and bottom wall; and
    lowering said upper die downwardly into said lower die, to thereby press said curd at a pressure of 4-5 kg/cm$^2$ for about 10 hrs. at an ambient temperature of 12°-15° C.

* * * * *